United States Patent [19]

Sorenson et al.

[11] Patent Number: 4,801,298

[45] Date of Patent: Jan. 31, 1989

[54] VARIABLE SIZED REUSABLE DIAPER

[76] Inventors: Wendy K. J. Sorenson, 360 W. Main; Judith N. Jackson, 291 N. 700 E., both of Payson, Utah 84651; Kevin J. Jackson; Cheryl Jackson, both of 942 N. 800 E., Genola, Utah 84655

[21] Appl. No.: 936,088

[22] Filed: Nov. 28, 1986

[51] Int. Cl.$^4$ .............................................. A61F 13/16
[52] U.S. Cl. ................................. 604/384; 604/378; 604/386
[58] Field of Search ............................... 604/370–373, 604/378, 385.1, 385.2, 386, 387, 391, 392, 394, 399, 358, 393, 395, 396–398, 379, 381, 402; 2/235–237, 325

[56] References Cited

U.S. PATENT DOCUMENTS

| | | | |
|---|---|---|---|
| 2,242,977 | 5/1941 | Marcos | 2/235 |
| 2,444,020 | 6/1948 | Markin | 2/235 |
| 3,658,065 | 4/1972 | Hirsch | 604/327 |
| 3,844,288 | 10/1974 | Kiela | 604/370 |
| 3,882,871 | 5/1975 | Taniguchi | 604/371 |
| 3,955,575 | 5/1976 | Okuda | 604/371 |
| 4,338,938 | 7/1982 | Seavitt . | |
| 4,397,645 | 8/1983 | Buell . | |
| 4,425,128 | 1/1984 | Motomura . | |
| 4,548,604 | 10/1985 | Ellsworth | 604/399 |
| 4,568,342 | 2/1986 | Davis . | |
| 4,662,877 | 5/1987 | Williams | 604/385 A |

FOREIGN PATENT DOCUMENTS

| | | | |
|---|---|---|---|
| 901202 | 5/1972 | Canada | 604/378 |
| 1205251 | 6/1986 | Canada | 604/370 |
| 2823562 | 1/1979 | Fed. Rep. of Germany | 604/379 |
| 1430747 | 4/1986 | United Kingdom | 128/287 |

OTHER PUBLICATIONS

Adjust-A-Waist Advertising Literature.
Sears Pinless Diaper Pant—Advertising & Photographs of Diaper.
Pampers Diaper—Photographs of Actual Diaper.
Huggies Diaper—Photographs of Actual Diaper.

Primary Examiner—C. Fred Rosenbaum
Assistant Examiner—Sharon Rose
Attorney, Agent, or Firm—Trask, Britt & Rossa

[57] ABSTRACT

A variable sized diaper, which is reusable, is disclosed. The diaper inlcudes an outer liquid impermeable panel having a generally hourglass configuration. The outer panel is sealedly connected about its perimeter to a corresponding inner panel having a substantially identical outer perimeter. The inner panel includes a fluid absorbent core, longitudinally positioned along the length of the diaper which is circumscribed by a plurality of side panels and waist panels which are constructed of liquid impermeable fabric. A conjunction of the inner panel and the outer panel defines a liquid permeable absorbent core which is substantially surrounded by a fluid impermeable hollow pocket or sack which extends about the entire circumference of the absorbent core. A "V"-shaped pile attachment strip is positioned on the frontmost regions of the diaper and is adapted to connect with a pair of hook fasteners one of which is positioned on each of the two wing-like portions of the rear portion of the diaper. The association of the hook and pile fasteners permits an adjustable placement of the diaper about the waist or girth of the infant. As the waist fitting region of the diaper is adjusted a corresponding adjustment in the leg openings of the diaper is obtained whereby the diaper may be adapted for use for an infant weighing between six to thirty pounds. The diaper also includes means of folding the frontmost portions of the diaper down so as to expose the naval region of the infant, thereby avoiding irritation of that region during its post-natal healing process.

10 Claims, 6 Drawing Sheets

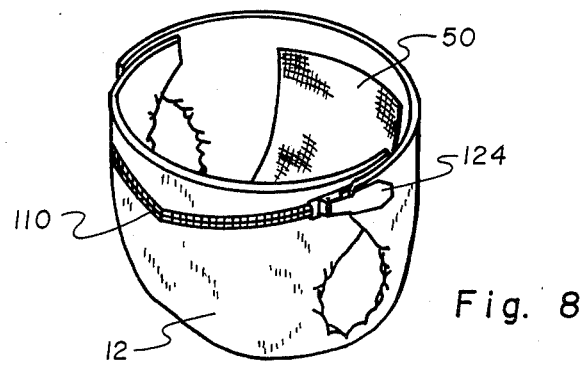
Fig. 8
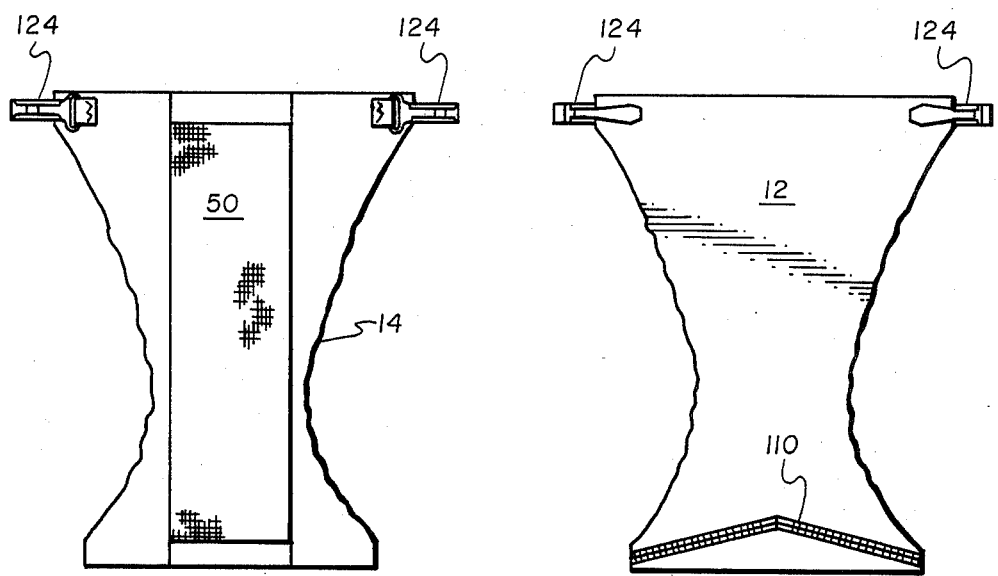
Fig. 9
Fig. 10

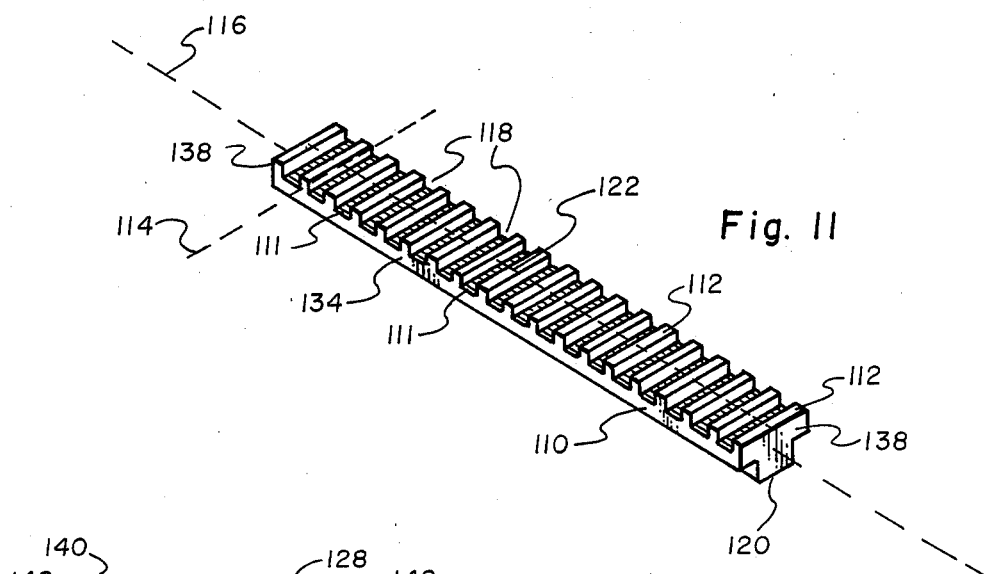
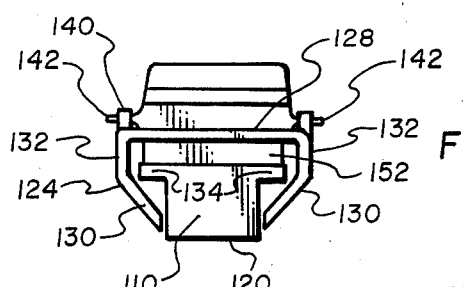
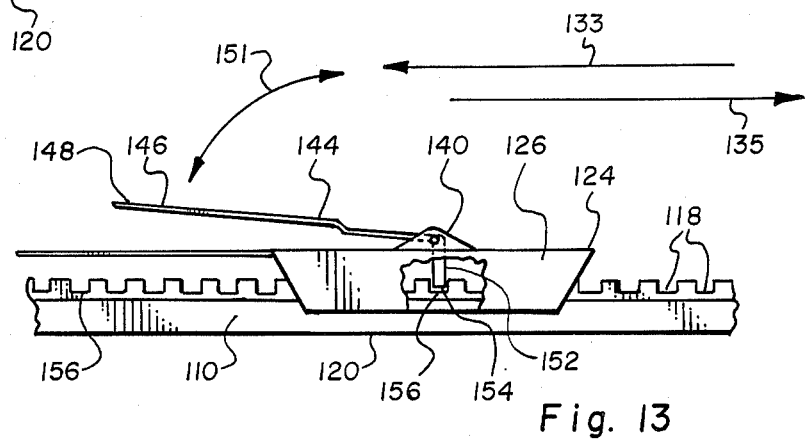
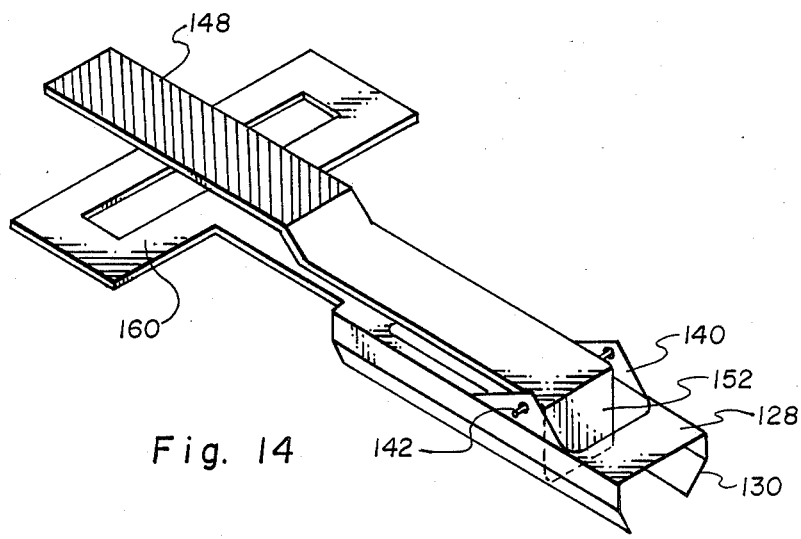

VARIABLE SIZED REUSABLE DIAPER

BACKGROUND OF THE INVENTION

1. Field: This invention relates to diapers. More specifically, the invention is directed to a diaper adapted to fit infants of various sizes. The invention is also directed to a diaper which is reusable.

2. State of the Art: Diapers have been known almost since the beginning of mankind. In their traditional configuration, a diaper consists generally of a rectangular-shaped piece of absorbent cloth or fabric. The fabric is folded generally into a triangular configuration which is adapted to be fitted about the lower abdominal region of an infant. In a conventional construction, the corners of the triangular-shaped folded fabric are joined one to another by means of various types of adhesive or connecting means. One widely used means is that of a safety pin. Of more recent vintage, is the use of adhesive-backed strips which are adapted to adhere, or connect to the fabric of the diaper. Also in use are various types of hook and pile fasteners. These latter type attachments are exemplified by those made commercially available by the Velcro Corporation of New York, N.Y., and traditionally sold under the trade designation "Velcro."

The structure of a typical fabric diaper is illustrated in U.S. Pat. No. 3,049,228 (Burnett). The Burnett diaper includes a generally rectangular sectioned fabric having a plurality of attachment means positioned about the corners of that fabric sheet. In use, the infant is positioned in a sitting orientation upon the generally central portion of the rectangular sheet. Thereafter, the ends or corners are drawn up around the infant's lower abdominal regions and are connected one to the other to form a generally sling-like structure. This structure is adapted to confine any fluids discharged from the infant. A similar rectangular-shaped structure is that shown in U.S. Pat. No. 3,141,461 (Farris).

Of more recent introduction, is the provision of a pair of generally semicircular leg openings along the sides of the rectangular diaper. These leg openings are generally placed in a symmetrical fashion about the longitudinal axis of that diaper. As shown in U.S. Pat. No. 2,649,858 (Le Bolt), the sides of the diaper fabric panel are cut-away at symmetrical locations about the longitudinal axis to define two generally demi-lune or semicircular bordered regions. These regions are sized to receive the legs of the infant wearer of the diaper. Upon the placement of the diaper about the infant, these semicircular regions conform about the circumference of the infant's leg. Due to the cutaway regions, the diaper fabric substantially encases the infant's leg. More specifically, the diaper encases that region of each leg proximate the lower abdomen of the infant.

The formation of the generally semicircular cut-out regions (as shown in Le Bolt) provides a diaper configuration which may be defined generally as a pair of outwardly extending lateral wings positioned both in the front and the rear sections of the diaper. These wings are conjoined to one another by means of an interposed longitudinally extending section.

A modification of the Le Bolt construction is that disclosed in U.S. Pat. No. 3,955,575 (Okuda). In the Okuda diaper, only one pair of laterally extending wings is formed, i.e. at the rear portion of the diaper. Instead of a pair of lateral wings on the front panel, the Okuda diaper is configured to have a generally rectangular section. In Okuda, the wings are adapted to extend about the waist from the back of the infant and toward the frontal abdominal region where they are connected to the rectangular panel by means of adhesive or attachment tabs. The Okuda construction avoids the use of cut-out sections for the leg regions. It appears to overcome such a need by fabricating the totality of the diaper from a tubular knit fabric which is stretchably conformable about the body of the infant.

Various other modifications of the dual-winged structure as shown in Le Bolt are those which are disclosed in U.S. Pat. Nos. Des. 275,518 (Larko) and 266,024 (Ternstrom et al.), and U.S. Pat. No. 4,196,733 (Elias-Geisseler).

With the advent of diaper constructions which utilize a large amount of paper fabric in their structure, many diapers are presently intended to be disposable. The typical disposable diaper avoids the need for the user to wash the soiled diaper. This aspect of the diaper contributes to its ease in use. A disposable diaper which is presently commercially available includes a plastic outer layer having a configuration generally identical to that described in U.S. Pat. No. 4,402,690 (Redfern). The outer perimeter configuration is generally similar to that disclosed by Le Bolt, i.e., it includes a pair of laterally extending front wings connected to a pair of laterally extending rear wings by means of a generally rectangular connecting section interposed therebetween. The interior of the diaper includes a generally rectangular-shaped high absorbency fiber fabric core which is positioned longitudinally, and parallel to the longitudinal axis of the diaper. The fiber fabric extends between each of the laterally extending wings. Positioned adjacent the longitudinal sides of the high absorbency core are a plurality of elastic-like members which are adapted to conform to the elongated connecting section of the diaper about the legs of the infant wearer. The diaper also includes a water permeable fabric which is positioned atop the high absorbency core. This permeable fabric is shaped to be generally identical to the outer plastic layer to facilitate its conforming or corresponding to that outer plastic layer.

The type of diaper sold under the trade designation "Pampers," is similar in construction to the diaper disclosed in Redfern. "Pampers" diapers include two opposing plastic sheet shields which are positioned over the ends of the liquid absorbent core and proximate the opposing end regions of the diaper. A pair of adhesive or tape-like tabs are mounted to each respective rear lateral wing, whereby the tabs are adapted to adhere to and thereby connet the rear wings with the front lateral wings upon the diaper being placed about the infant's lower abdominal region.

The configuration of a diaper has as its central objective, the provision of a fabric member which is adaptable to be wrapped around the infant and seal itself against the infant's body to prevent the leakage of waste deposited on the diaper. More specifically, a diaper is designed to preclude the escape of liquid outward between the interface of the diaper with the infant's body. The regions of interface which are of most importance in this regard are the juncture of the legs with the abdomen and about the infant's waist.

The dual-winged diaper constructions, as described above, are fitted typically with elasticized members. These elasticized members are generally positioned within and about the diaper's longitudinally extending central region. These elasticized members are directed toward conforming that region to the shape of the infant's legs and hopefully avoiding the leakage of waste. Diapers generally include a liquid permeable layer which is abutted against the infant's legs by the action of the elastic members. In the Redfern construction, the closure tabs, which hold the diaper in its fitted configuration, are adapted in large part to constrict the circumference of the waist portion of the diaper. The closure of the region about the legs is left largely dependent upon the action of the elastic members to adhere the diaper fabric against the infant's legs sufficiently to retard leakage. As a result, the leg openings by and large do not fit against the infant's legs comfortably. The elastic members must restrict the openings sufficiently to overcome a fabric structure which is generally resistant to conforming itself in a sealing relationship with the infant's legs. Resultingly, excessive force must be applied to the leg openings in order to achieve a seal. This excessive force often results in the leg openings being unduly constricted about selected regions of the infant's legs.

Other diaper configurations have attempted to resolve the leakage problem by the installation of a fluid channel between the high absorbency member and the perimeter of the diaper itself. As shown in U.S. Pat. No. 2,828,745 (Deutz), a diaper may consist of a waterproof outer fabric fitted on its inner surface with a high absorbency core. The region between the core and the perimeter of the plastic region defines a generally open channel. Liquid, which may escape being absorbed by the core, is channeled about the circumference of that core until it contacts a region of the core which has yet to absorb its maximum quantity of fluid. Thereafter, that fluid is absorbed within that unsaturated core region. Constructions such as the "Pampers" diaper employ a waterproof shield about the waist region to avoid leakage at that interface.

Notwithstanding the prior attempts to construct a diaper which is leakproof, the present diapers to one degree or another have difficulty in assuring totally leakproof operation.

The heretofore described diaper configurations are typically adapted for use with an infant of selected size and weight. The more flexible diaper constructions are adapted for use with infants within a preselected weight range, e.g. 6-14 pounds. These latter diapers pose problems when attempts are made to fit the diaper to an infant which is outside of the fairly narrow size range. Of interest in an ideal or optimized diaper construction is its ability to fit an infant between 6 and 30 pounds. Present diapers require that the user switch the size of diapers used at intervals as the infant grows. Stated in other words, none of the above-described diapers appear to be adapted for long term adjustability whereby the infant may be serviced from the time he is born until the time he is no longer in need of a diaper.

One of the concerns which is typically not addressed by most conventional diaper structures is the sensitivity or susceptibility to injury of the newborn infant about its navel region. When the child is born, a portion of the lower abdomen which formerly was connected to the umbilical cord is highly sensitive. In most diaper constructions, the diaper fails to take into account this sensitivity. In U.S. Pat. No. 4,230,113 (Mehta), a diaper construction is shown wherein a "V"-shaped slot is removed from a conventional rectangular-shaped diaper. The slot exposes the navel region of the infant's lower abdomen when the diaper is in position about the infant. While this construction does address the problem of the sensitivity of the navel region, the use of the diaper is substantially prejudiced. As the region of the infant's body heals and becomes somewhat insensitive and therefore capable of being covered by the fabric of a diaper the inclusion of the Mehta slot may provide a means for liquid escape from the diaper. The problem is further compounded by the location of the slot being in a region of the infant's liquid discharge.

SUMMARY OF THE INVENTION

The instant invention discloses a diaper which is both reusable and adjustable to fit an infant over a wide size range. The diaper includes an outer panel having a rear and front portion. A pair of laterally extending wings are positioned on the rear portion of the diaper. A second pair of laterally extending wings, which forms the front portion of the diaper, is connected to the rear wings through -means of an elongated connecting strip. The diaper is disposed about an imaginary longitudinal axis and is configured to be symmetric about that axis. The outer panel is formed of a liquid impermeable fabric which may be air permeable. This fabric is generally not stretchable.

An inner panel of the diaper is formed in a configuration which is substantially identical to that of the outer panel, i.e., it consists of a pair of front laterally extending wings joined to a rear pair of laterally extending wings through means of a elongated connecting strip positioned therebetween. The outer panel, as well as the inner panel, are configured to define a generally hourglass plan view shape. The inner panel includes a generally elongated fluid absorbent layer or core which is positioned substantially centrally within the inner panel and parallel to the longitudinal axis of that panel. This central core is typically fabricated of a fabric, which is adapted to absorb and retain liquid. Circumscribing the entire perimeter of that central core is the outermost section of the inner panel. This outermost section is fabricated from a liquid impermeable fabric which may also be air permeable. The fabric is generally not stretchable. The outermost section of the inner panel extends about the total circumference of the inner core, not only along the sides of the core, but furthermore across both ends of the core.

The inner and outer panels are connected to one another by positioning the inner panel substantially atop the outer panel thereby aligning the perimeters of the two corresponding panels. The panels are thereafter sewn one to the other about the perimeters of the panels. The association of the two panels forms a sealed sack-like in a pocket-like structure having a hollow interior cavity which substantially may only be accessed through the porous fabric of the absorbent inner panel core.

The elongate connecting strips of both the inner and outer panels, in conjunction with the front and rear wings of those panels define a pair of oppositely positioned, generally semi-circular openings positioned on the side perimeters of the panels. At least two elastic-like strips are positioned along the interface between the inner and outer panel, within that section defined as the elongated connecting strip. These elastic strips are positioned parallel to the longitudinal axis of the diaper and sewn into the corresponding inner or outer panels. The elastic strips are sewn to a flat fabric panel while the strips are in an extended or stretched orientation. Upon a release of the strips, the elastic nature of the strips operates to compress the panel into a series of fabric gathers. The elastic strips form an automatic adjustment of the leg opening portion of the diaper whereby he diaper adjusts itself to the size of the infant's legs and forms a snug fit between the diaper and those legs.

Positioned on the front portion of the outer panel is an attachment strip. In a preferred embodiment, this attachment strip is formed in a generally "V"-shaped configuration. The attachment strip is positioned substantially symmetrical about the longitudinal axis of the outer panel, i.e., the arms of the "V"-shaped connecting strip extend from a central region located on that longitudinal axis outwardly towards the front lateral extending wings. When viewed in plan view, the "V"-shaped member may be positioned so as to extend from a central region of the panel outwardly to the tips of the outer panel wings.

Positioned proximate the upper regions of the laterally extending rear wings are a pair of connecting fasteners. The connecting fasteners are each positioned on the outermost portions of their respective wings. In use, the connecting fasteners are adapted to be wrapped about the waist of the infant and interact with the attachment strip positioned on the front portion of the outer panel.

Due to the orientation of the connecting fasteners and the "V"-shaped connecting strip being positioned substantially symmetrical about the longitudinal axis of the front panel, the diaper is adapted to be fitted about a considerable size range of infants. The orientation of the fastening strips permits the user to adjust the waist measurement of the diaper, whereby the fluid impermeable fabric of the inner panel is abutted against he infant's waist to form a liquid proof belt-like fitting about the infant's waist. Furthermore, as the rear wings are advanced along a slanted arm of the "V"-shaped attachment strip positioned on the front portion of the diaper, the size of the opening for the legs is also adjusted correspondingly to snugly wrap the leg opening of the diaper about the infant's leg.

The formation of the "V"-shaped connecting strip on the front portion of the diaper defines a border or barrier which permits the user to fold under the portion of the outer and inner panels which is between that connecting strip and edge of the diaper. In its folded-under configuration the diaper defines a "V"-shaped structure suitable for placement upon the infant which avoids a placement of fabric over the infant's navel. This feature is of critical importance when the diaper is used on a newborn infant whose navel region has yet to heal sufficiently to tolerate a placement of a fabric thereover. As the infant heals, the folded under portion may be unfolded to return the diaper to a configuration which positions a portion of the diaper sufficiently above the infant's lower abdominal region to avoid waste discharge through the waist region of the diaper.

BRIEF DESCRIPTION OF THE DRAWINGS

FIG. 2 also illustrates the placement of hook and pile-type fasteners on the back lateral extending wings.

FIG. 8 is an elevational perspective view of a second embodiment of the diaper wherein a dentil surfaced attachment strip forms a portion of the connection means.

FIG. 9 is a plan view of the inner panel of the diaper of FIG. 8.

FIG. 10 is a plan view of the outer panel of the diaper of FIG. 8.

FIG. 11 is an elevated perspective view of the dentil surfaced attachment strip shown in FIG. 8.

FIG. 12 is an end view of the attachment strip of FIG. 11 in association with a attachment strip.

FIG. 13 is a side view of the attachment strip of FIG. 10 in association with a attachment clip.

FIG. 14 is a perspective view of the attachment clip shown in FIGS. 12 and 13.

DETAILED DESCRIPTION OF THE DRAWINGS

A diaper of the instant invention includes a outer panel, generally 12, which is connected to an inner panel, generally 14.

Figure 15:
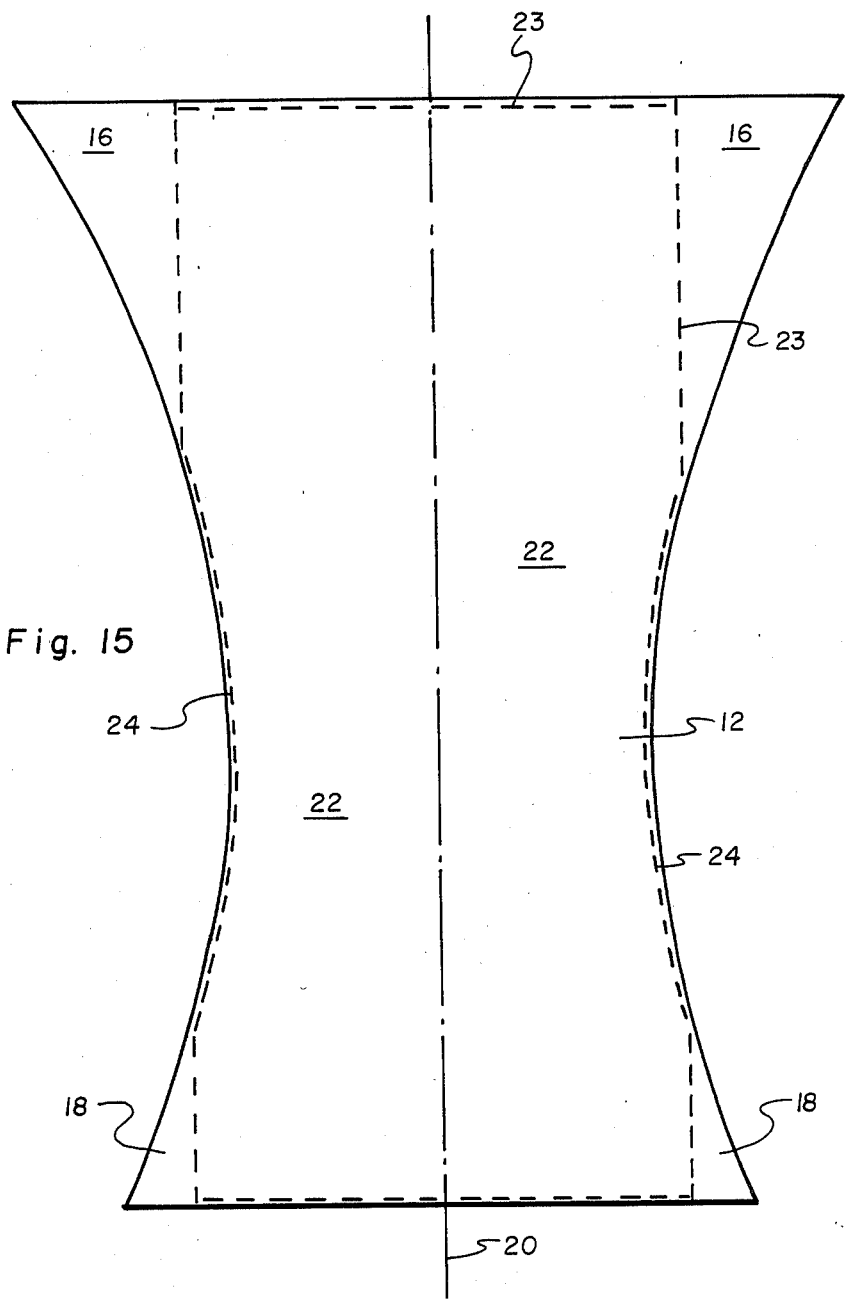
FIG. 15 is a plan view of the outer panel of the diaper of this invention.
Figure 16:
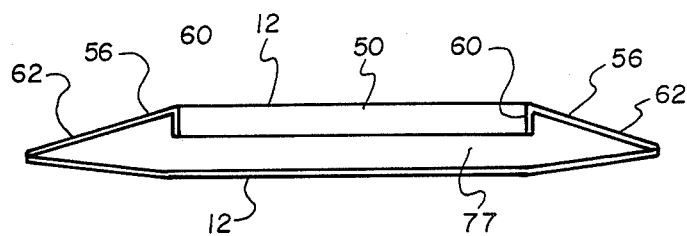
FIG. 16 is a cross-sectional view of the diaper shown in FIG. 7 taken along sectional lines 16—16.
Figure 17:
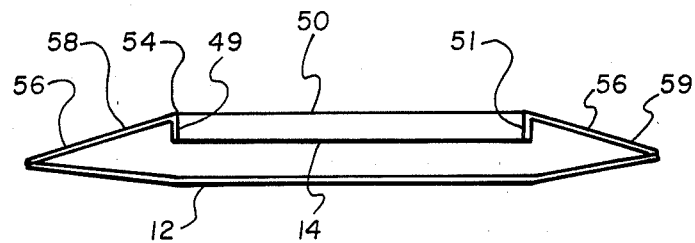
FIG. 17 is a cross-sectional view of the diaper shown in FIG. 7 taken along sectional lines 17—17.

Outer panel 12 consists of a fabric section which is configured in a generally hour glass shape. As shown in FIG. 15 (in dotted section), panel 12 may be viewed as being composed of a pair of laterally extending wings, generally 16, which are positioned about the back portion of the diaper and a pair of laterally extending wings 18 which are positioned about the frontmost portions of the diaper. Each of the wings 16 and 18 extend outwardly from the diaper's longitudinal axis 20. Furthermore, each pair of wings 16 and 18 is positioned substantially symmetrical about the axis 20. The pairs of wings 16 and 18 are connected to one another by a fabric section designated generally 22. As shown in FIG. 15 the section 22 is of an elongate configuration, and is generally rectangularly shaped. The generally linear sided perimeter 23 of section 22 is interrupted along two portions thereof by two substantially semicircular or arc-like segments 24. The arc-like perimeter sections 24 are generally positioned symmetrical about longitudinal axis 20. Sections 24 are configured to adapt the structure of the diaper to the general configuration of a infant's legs permitting the section 22 to be wrapped around those legs and to form a tight seal against the legs.

Outer panel 12 is generally formed of a liquid impermeable fabric. In preferred embodiments this fabric may be nylon having thereon a coating which renders the nylon impermeable to liquid. In some embodiments, the fabric may be permeable to air. A preferred construction utilizes a fabric made commercially available under the trade designation 100% duPont coated Nylon. Those fabrics which are available commercially under the trade designations Gore-Tex ® and Entrant may also be used.

The inner panel 14 is shaped and dimensioned similar, if not identical, to the shape formerly described for the outer panel 12, i.e., it consists of a pair of outwardly extending lateral wings 16A positioned proximate the rearmost portions of the diaper. Wings 16A are connected to a second pair of lateral extending wings 18A on the frontmost portions of the diaper. Wings 16A and 18A may be interconnected by means of a longitudinal connection strip-generally 22A which is interposed therebetween. Strip 22A corresponds in structure and form to strip 22 of outer panel 12 and includes corresponding curved perimeter segments 24A. Dimensionally the shape of the inner panel is substantially identical to that formerly described for the outer panel 12.

In a preferred construction the diaper is adapted to fit infants weighing from 6 to 30 pounds. In this construction the width of the diaper, along the edge identified generally as 30 is dimensioned to be approximately 16½ inches. The opposing width, along edge 32, is dimensioned to be approximately generally as 34, is dimensioned to be approximately 17½ inches. In this preferred construction it may be noted the width along edge 32 is dimensionally smaller than the width along edge 30.

The generally arc-like perimeter regions 24 of longitudinal section 22 are not exactly symmetrical about a lateral axis generally 39 which extends perpendicular to the longitudinal axis 20 of the diaper.

In the preferred construction just described the width 35A of the diaper, at the location designated generally 35, is approximately 5½ inches. As shown in FIG. 15, the perimeter segments 24 form smooth concave curves which begin at the tips of the wings 16, curve inwardly to the location 35 and then curve or flare outwardly to the tips of wings 18. In the preferred construction described, the axis 39 is positioned approximately ten (10) inches from the edge 30 and approximately five (5) inches from the edge 32.

Positioned on the frontmost portion of the diaper, i.e., proximate wings 18 is a pile-like attachment strip 40. In a preferred embodiment this fabric strip 40 is a formed in a generally "V"-shaped configuration. Strip 40 is positioned on the diaper to be symmetrical about longitudinal axis 20. The wings 42 of the attachment strip are positioned to extend from the longitudinal axis 20 outwardly and intercept the tips 44 of the wings 18. Viewed from a second perspective, the attachment strip 40 extends in an angulated fashion from the tips 44 of the laterally extending wings 18 inwardly until connecting with or intercepting the imaginary longitudinal axis 20. The distance separating the edge 32 of the diaper and the apex 46 of the "V"-shaped attachment strip 40 is configured to permit that portion of the diaper circumscribed by the edge 32 and the two edges 47 of the pile attachment strip 40 to be easily folded under. The attachment strip 40 forms a boundary or edge of sufficient rigidity that the portion of the panels 12 & 14 between that boundary and edge 32 may be easily folded under to form a "V"-shaped edge 33 on the upper front of the diaper.

Figure 5:
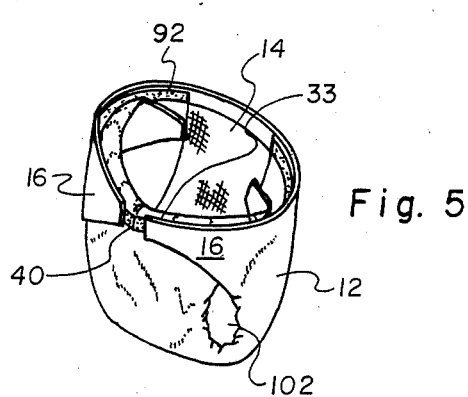
FIG. 5 is an elevated perspective view of the diaper of the instant invention illustrating the formation of a "V"-shaped, "turned over" section of the diaper adapted for retaking the diaper out of contact with the navel region of the infant.
Figure 6:
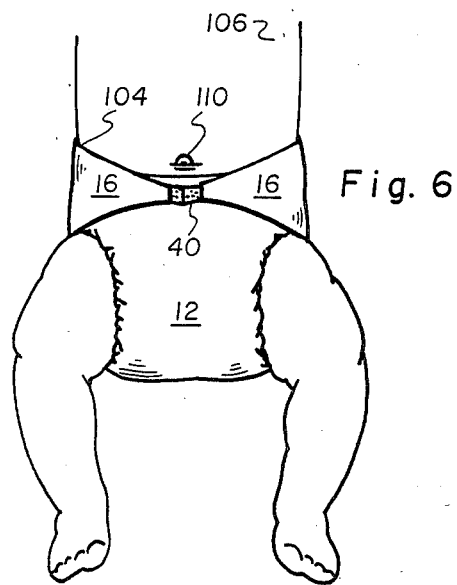
FIG. 6 is a frontal view of the diaper shown in FIG. 5 detailing the placement of the diaper about an infant.

In a typical construction the distance identified generally as 49 is approximately 2½ inches in length. As shown in FIG. 5, the upmost region of the front of the diaper, i.e. that portion of the diaper between the edge 32 and the edges 47 of the pile strip 40 may be folded down toward the axis 39 of the diaper, thereby permitting the diaper to be placed on the infant without producing a contact of the diaper with the navel region 110 of the infant. This placement is shown in FIG. 6. As the infant's navel region heals sufficiently to permit contact with fabric, the diaper may thereafter be left in its unfolded configuration thereby defining a high waisted, maximized liquid retention means. The folded under configuration of the diaper permits it to be worn by a newborn infant whose naval region may be highly sensitive prior to its having healed after the removal of the umbilical cord.

Figure 2:
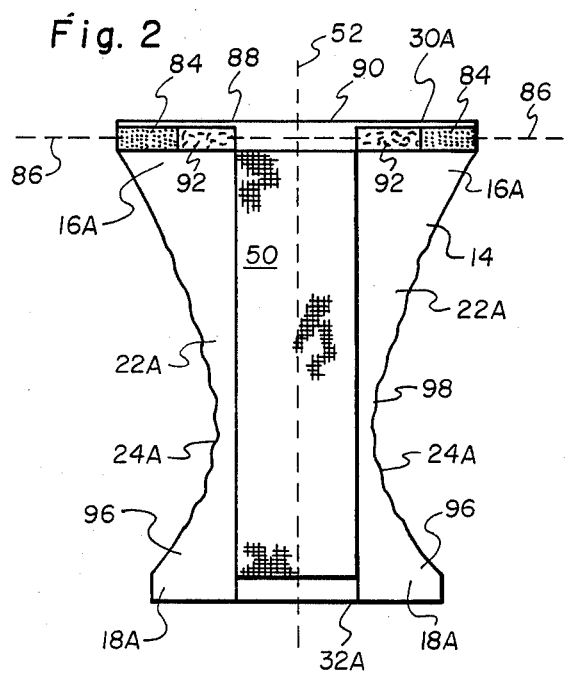
FIG. 2 is a plan view of the inner panel of the diaper illustrating the placement of the central absorbent core in conjunction with the circumscribing liquid impermeable outer sections.
Figure 3:
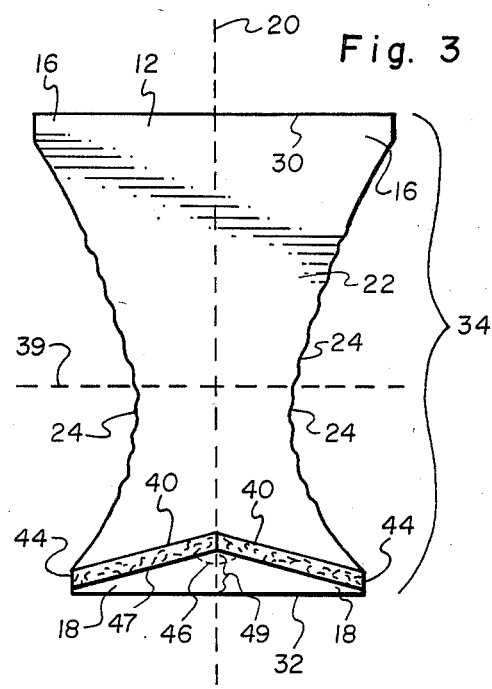
FIG. 3 is a plan view of the outer panel of the invention showing the placement of the "V"-shaped pile attachment strip on the frontmost portions of the diaper.
Figure 4:
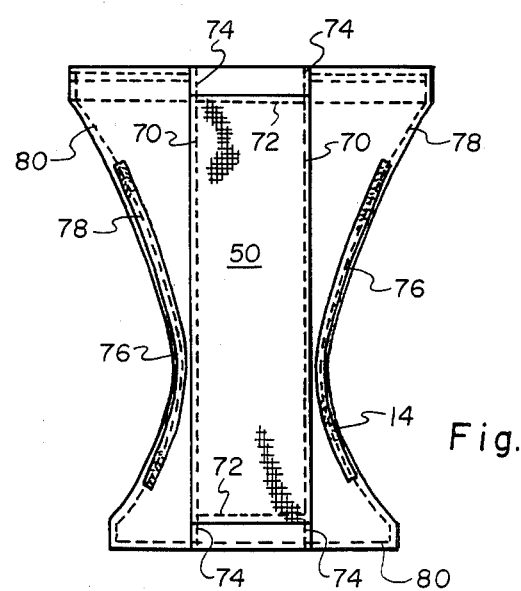
FIG. 4 is a plan view of the reverse side of FIG. 2 illustrating the placement of elastic strips longitudinally about the surface of the interior panel of the diaper in conjunction with the placement of the central core.
Figure 7:
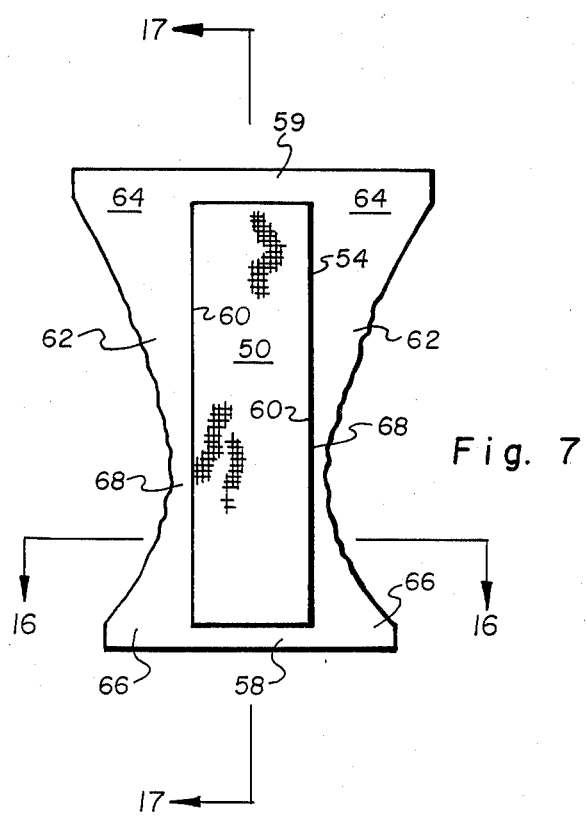
FIG. 7 is a plan view of the diaper shown in FIG. 2 having the attachment strips removed for purposes of clarity.

The inner panel 14 as shown to advantage in FIGS. 2, 4 and 7, includes a central, elongate, generally rectangular absorbency panel or core 50. Core 50 is positioned symmetrically about the longitudinal axis 52 of the panel 14. The core 50 may be formed of any absorbent fabric such as flannel, gauze padding, sponge cloth or any other type of fabric which is capable of absorbing and retaining liquid. Furthermore, the core 50 may be formed of multiple layers of absorbent fabric.

As shown in FIG. 7 the core 50 is circumscribed about its entire perimeter 54 by an outer fabric section generally 56. Section 56 is formed of a liquid impermeable material, substantially similar, if not identical, to the type of fabric used to fabricate the outer panel 12.

The section 56 may be formed of four separate and distinct subpanels: A rectangular shaped end or waist-type panel 58 is positioned upon an end 49 of the core 50 proximate the frontmost region of the diaper. A corresponding rear waist panel 59 is positioned on the opposing end 51 of the absorbent core 50. Positioned along each side 60 of the absorbent core are side panels 62 which each include a rear wing 64 and front wing 66 connected therebetween by a elongate connecting strip 68. As shown in FIG. 4 the side panel 68 may be connected to the inner core 50 by means of stitching or sewing the side panels directly to the core 50 along a generally straight line designated 70. The waist panels both rear and front, i.e., 58 and 59 also may be stitched to the core 50 along lines 72 as well as stitched to their respective corresponding side panels 68 along lines 74.

As shown in FIG. 4 a pair of elastic strips 76 are positioned along the edge 78 of each of the side panels 68. Elastic strips 76 are mounted on the side panel 68 in a stretched, i.e., tensioned, orientation whereby upon their release from that stretched orientation the elasticized strips 76 effect a contraction or gathering of the fabric side panels 68. As shown only two elastic strips 76 are positioned substantially symmetrically about the longitudinal axis 52 of the interior panel 14. It should be understood that in other embodiments a plurality of such strips may be positioned along each of the side panels 68.

Inner panel 14 may be connected to inner panel 12 by aligning the inner panel 14 over and above outer panel 12 to substantially align the perimeter of the inner panel with that of the outer panel. Thereafter the two panels are connected by stitching or sewing about the aligned perimeters, for example as shown along line 80. Preferably, the inner panel 14 as shown in FIG. 4 is face up while the two panels 12 and 14 are sewn together. A portion of the perimeter is left unsewn, whereby the construction thus forced may then be reversed, i.e. inverted inside out to form a finished structure wherein the edges of both inner panel 14 and outer panel 12 are positioned within that structure. This reversal or inverting inside out is accomplished by a technique well known in the sewing arts, i.e. by pulling the diaper through the unsewn portion of the perimeter. After the two panel construction is inverted, the unsewn perimeter region is sewn up to form a sealed diaper structure defining a hollow cavity 77 within. The joining of panels 12 and 14 defines a sack or pocket-like structure wherein the outer walls of that sack are formed by water impermeable yet air permeable fabric. The only access to the interior cavity of that sack is through the elongate liquid absorbent core positioned within the central region of the hourglass shaped sack; stated otherwise, the impermeable sack defines a hollow interior cavity which is made accessible to liquid solely through the absorbent core. Once liquid enters the interior cavity, it can only exit through that same absorbent core.

Positioned on the rearmost wings 16A of the interior panel 14 are a pair of hook-like fastener strips 84. As shown in FIG. 2 these strips 84 may be of an elongate configuration and are positioned along an imaginary lateral line 86 which is oriented perpendicular to the longitudinal axis 52 of the diaper panel 14. The hook strips 84 are positioned proximate the edge 88 of the diaper which forms the edge 30A of the panel 14. The hook strips are positioned near the tips of the lateral wings 16A.

A corresponding pile-like connecting strip 92 may be positioned proximate or adjacent to each of the hook strips 84. The placement of these pile connecting strips 92 facilitates the overlapping of that portion of the wing having thereon the hook strip 84 over and above the pile strip 92. As a result the pile strip 92 and the hook strip 84 are held in a detachable association. This construction precludes the hook strip 84 from contacting the pile-like strip 40 positioned on the frontmost portion of the outer panel 12. This orientation is beneficial when the diaper is placed in a washing machine or other cleaning apparatus wherein it is critical that the inner panel surface 14 be exposed to the cleaning agents within that apparatus. If the hook-like portions 84 are maintained free of any association with the pile strips 92 they may interconnect with the pile 40 and thereby prevent or isolate the surface of inner panel 14 from contacting effectively the cleaning agents within the washing apparatus.

Figure 1:
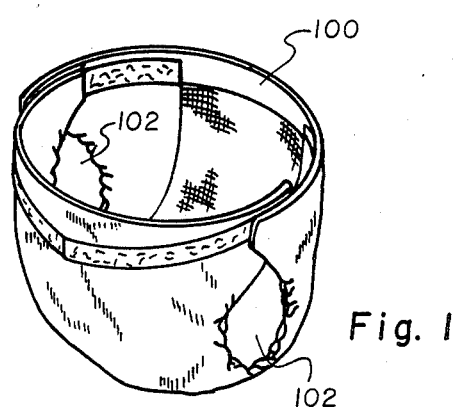
FIG. 1 is an elevated perspective view of a diaper of the instant invention detailing the placement of a pile attachment strip on the frontal regions thereof.

As shown in FIG. 1, the assembly of the diaper permits the positioning of the hook strips 84 in connection with the "V"-shaped pile strip 40 positioned on the front wings 18 of the outer panel 12. The connection of those hook strips 84 with the pile 40 defines an adjustable waist girthing structure which also permits a corresponding adjustment of leg openings 102. As shown in FIG. 6 the orientation of the rear wings 16 and 16A may be advanced along the length of the arms 42 of the attachment strip 40 to form a snug fit against the abdominal walls 104 of an infant 106. When worn, the diaper positions a liquid impermeable waistband about the infant's waist which hinders if not precludes the passage of liquid waste upward and out of the diaper structure. As the wings 16/16A are advanced along the length of the pile arms 42 not only is the waist or the girth of the diaper diminished but furthermore, the circumference of the leg holes 102 is also reduced proportionally. Due to the interaction of the curved perimeter 24/24A elongate section 22 and 22A and the novel angled orientation of the attachment strip 40, this construction facilitates an adjustment of the waist with a corresponding and appropriate adjustment of the leg holes 102. As a result, not only is the diaper snugly fitted against the infant's waist but furthermore it is also snugly fitted against the infant's legs. In use, the diaper forms a liquid-tight seal of the diaper against all possible leakage openings, i.e. all of the interfaces between the diaper and the infant are sealed. Furthermore, this seal is obtained without the need of applying excess force to the leg openings through means of the elastic strips mounted proximate the leg openings.

FIGS. 8-14 illustrate a second embodiment of the diaper of this invention. The second embodiment includes an attachment strip 110 which is a generally semi-rigid elongate member. Strip 110 includes a plurality to upright or upstanding ribs 112 mounted on its upper surface 111. As shown in FIG. 11, each of the ribs 112 is a generally elongate member having a substantially rectangular cross section. The longitudinal axis 114 of each rib 112 is oriented perpendicular to the longitudinal axis 116 of the strip 110. All of the ribs 112 are identical in shape and dimension. The ribs 112 are placed equally spaced along the surface 111 of strip 110 thereby defining a recess well 118 between each pair of ribs 112. All recess wells 118 are identical in shape and configuration. The ribs in association with surface 111 defines a generally dentil configured structure. The strip is fabricated from a semi-rigid yet flexible material such as plastic.

As shown in FIG. 8, a pair of strips 110 may be mounted on the front surface of the outer diaper panel 12. The strips are oriented in a "V" configuration substantially similar, if not identical, to the placement of the pile strip 40. The ribs are positioned to face outwardly from the surface of the panel 12, i.e. the bottom surface 120 of the strip 110 abuts against the surface of panel 12. The strip 110 may be mounted on the panel 12 by sewing. Preferably the strip is mounted by a sewn stitch positioned along the dotted line designated 122 in FIG. 11.

On each of the wings 16A of the inner panel 14, the hook attachment fasteners 84 are replaced in this second embodiment by a pair of clip-like structures 124. As shown in FIGS. 12-14, structures 124 include an elongate carriage 126 which includes a planar platform 128 having a curved flange or lip 130 which extends downwardly from each of the opposing sides 132 of that platform 128. The lips 130 are adapted to fit around flanges 134 defined by strip 110. Due to the interrelationship of lips 130 and flanges 134, the carriage may slide along the length of strip in a reciprocative fashion as shown by arrows 133 and 135. The strip 110 is of constant diameter and configuration along its entire length. The clip 124 may also slide off the strip 110 at either end 138.

Fitted on the surface of platform 128 is a pair of spacedly positioned upright supports 140. Each support 140 defines an aperture therein configured to receive an elongated pivot pin 142 of a lever 144. As shown, lever 144 is a generally elongate member having a handle 146 on one end 148. Positioned on the opposite end 150 is an extension 152. Extension 152 includes an end 154 thereof dimensioned to be received within a recess well 118 defined by ribs 112.

As shown in FIG. 13, the lever 144 pivots about the pivot pins 142 in a vertical plane in both a clockwise and counter-clockwise direction, as indicated by arrow 151. As lever 144 is pivoted in a counter-clockwise direction extension 152 is pivoted into a recess well 118, and the end 154 of extension 152 is abutted against the floor 156 of the recess well 118. The extension 152 is of a sufficient length that the extension exerts a compressive action on that floor 156. Due to the semi-rigid nature of the fabrication material of strip 110, the association of the extension fitted carriage 124 and the strip 110 is held in a firm yet releasable union upon the handle 146 being positioned the location shown in FIG. 13. Since the extension is positioned in abutment against the side of a rib 112, any further sliding of the carriage 124 along strip 110 is precluded until the lever 144 is disengaged.

The clip 124 is preferably fabricated from a rigid material such as metal or a hardened synthetic material, e.g. plastic.

Fitted on carriage 126 is an anchoring member 160. This anchor 160 is configured to permit the clip 124 to be mounted on the tips of the wings 16 of panel 12 or alternatively on wings 16A of panel 14. The placement of the clip 124 on the diaper corresponds to the placement of the hook attachment 84 as shown in FIG. 2. In one method, the handle 160 may be mounted on wings 16 or 16A by stitching or sewing.

To operate the attachment means, the user places the carriage 124 on the attachment strip 110 by aligning lips 130 and flanges 134. The carriage 124 is then moved along the length of that strip 110 until the desired diaper fit is obtained. In moving the carriage 124 along that strip 110, the extension 152 is held out of contact with ribs 112. To lock the carriage 124 in position, the lever 144 is rotated counter-clockwise in order to bring the end 154 of extension 152 into a recess well 118. As the lever is rotated further, the end 154 pushes against the floor 156 and compresses it. This compressive action together with the structural configuration of the clip 124 forms a manually releasable but firm union of the clip 124 and strip 110. This union precludes a displacement of the carriage 126 along the strip 110 until the lever is rotated in a clockwise direction, thereby disengaging the extension 152. Thereafter, the clip 124 may be further adjusted, or alternately, the clip may be slid off the strip 110 permitting the disassociation of the respective pair of wings 16 and 18 which were formerly associated when the clip 124 was engaged with the strip 110.

Since the strip 110 is semi-rigid in construction, it likewise offers the advantages of a border for folding the "V"-shaped region of the diaper to avoid contact with the infant's navel.

As may be observed from the above detailed structure and mode of operation, the instant invention describes a diaper which is constructed of materials which are reusable and washable.

The provision of the "V"-shaped pile in conjunction with the laterally extending hook strips positioned on the rearmost wings facilitates a connection means adapted to adjust simultaneously the waist as well as the leg holes of the diaper sufficiently that one diaper may fit an infant between 6 to 30 pounds. As a result the instant invention provides a diaper which is adaptable for a infant's use throughout the life of the infant wherein a diaper is necessary. Furthermore, the diaper is adapted to address provisionally the needs of an infant whose navel region has yet to heal sufficiently to permit contact with a fabric. Also the diaper addresses the need of providing a sufficiently expansive front section of the diaper to contain fluid within the diaper subsequent to the healing of the navel. The diaper is adapted to be foldable so as to retain itself away from the navel during its sensitive healing process. Subsequent to that process being accomplished the diaper may be unfolded and adjusted to provide a sufficiently high waistband to seal against the waist to preclude leakage.

Since core 50 is positioned proximate those regions wherein body fluids are being discharged such liquids are immediately absorbed into central core 50. Upon those liquids being absorbed into the core 50, any excess liquid is discharged outwardly from the core into the liquid impermeable sack formed by the side panel 68, waist panels 58 and 59, and the outer panel 12.

In effect the instant invention defines a liquid impermeable sack or pocket which is positioned about substantially the entire circumference of the access opening of that sack i.e. the absorbent core 50. The only region of the absorbent core 50 which is not surrounded by a waterproof pocket is that region which is held in direct abutment or contact against the skin of the infant. Therefore any liquid which is received on the absorbent core 50 must either be absorbed by that core, be retained against the skin of the infant or be directed outwardly into the fluid impermeable sack. The width of the side panels 68 and the core 50 is adjusted such that the core 50 is positioned proximate the infant's excretory organs, i.e. the side panels 68 are positioned such that the possibility of liquids being discharged thereon is remote. This construction not only channels the liquid waste directly to the absorbent core and the interior of the impermeable sack but furthermore, precludes any liquid discharged onto the core 50 from being transmitted to the perimeter 98 of the diaper across the impermeable outer section of the inner panel 14. This new diaper construction substantially avoids any possibility of fluid being transmitted to outer garments of the infant which may be positioned over the diaper.

Though the above disclosure has been directed to embodiments of the invention relating to infant diapers, it should be understood that the invention is equally useful in all environments wherein a diaper is required, e.g. geriatric patients and the handicapped.

Those skilled in the art will recognize that the embodiments hereinbefore discussed are illustrated of the general principles of the invention. The embodiments herein described are not intended to limit the scope of the claims which themselves recite what applicants regards as their invention.

We claim:

1. A variable sized, reusable diaper comprising:
   an outer panel having a first perimeter, said outer panel being disposed about a first imaginary longitudinal axis; said outer panel having a back portion possessing first and second laterally extending wing portions and a front portion possessing third and fourth laterally extending wing portions; said outer panel being fabricated from a liquid impermeable, washable fabric;
   a "V"-shaped pile attachment strip mounted on said front portion of said outer panel, said attachment strip extending from an edge of said first wing to said longitudinal axis and from an edge of said second wing to said longitudinal axis;

an inner panel having a second perimeter, said inner panel being disposed about a second imaginary longitudinal axis, said inner panel having a back portion possessing a fifth and a sixth laterally extending wing corresponding in configuration to said first and second wing of said outer panel, said inner panel also having a front portion possessing a seventh and an eighth laterally extending wing corresponding in configuration to said third and fourth wings of said outer panel, said inner panel and outer panel being connected one to another about their respective corresponding perimeters, said inner panel being composed of a liquid absorbing elongated porous fabric strip positioned parallel with said second longitudinal axis and a liquid impermeable sheet mounted to circumscribe said liquid absorbing strip an association of said inner panel and said outer panel defining a hollow sealed impermeable sack having an interior cavity; said cavity being accessible through said porous absorbent strip wherein liquid contacting said absorbent strip in excess of said strip's ability to absorb said liquid is directed to said interior cavity and retained therein by said impermeable sack;

a pair of elongated loop fastener strips, one of said strips being mounted on each of said fifth and sixth wings of said inner panel, said fastener strips being adapted to form a manually releasable union with said pile attachment strip, wherein said fastener strips are positioned perpendicular to said second longitudinal axis.

2. The diaper according to claim 1 wherein said liquid impermeable sheet is fabricated from an air permeable fabric.

3. The diaper according to claim 2 wherein said liquid absorbing strip is fabricated from flannel.

4. The diaper according to claim 1 wherein a pair of elastic strips is mounted between said inner and outer panel parallel to said longitudinal axes.

5. A resuable, variable size diaper comprising:
an outer panel having a first perimeter, a pair of first front laterally extending wing sections and a pair of back first laterally extending wing sections; said outer panel being fabricated from a liquid impermeable, washable fabric;
a first elongated connection strip, interposed between said first back and front wings;
an inner panel having a second perimeter substantially identical to said first perimeter of said outer panel, said inner panel being joined to said outer panel along their corresponding respective perimeters, said inner panel including a pair of second front laterally extending wing sections and a pair of second back laterally extending wing sections, a second elongated connection strip being interposed between said second front and second back wing sections, said inner panel including a centrally positioned liquid absorbent fabric panel having a third perimeter, wherein said absorbent fabric panel is circumscribed about its third perimeter by a liquid impermeable fabric panel wherein said joining of said outer panel with said inner panel constitutes a hollow cavity, substantially liquid retaining sack composed of liquid impermeable walls except for that portion of said sack's walls defined by said liquid absorbent fabric panel, wherein said sack's hollow cavity is accessed substantially solely through said liquid absorbent panel whereby liquid which contacts said liquid absorbent panel is absorbed into said absorbent panel and thereafter into said sack; whereby said liquid is precluded from flowing outward from said absorbent panel to said inner panel and said outer panel perimeter;
fastening means associated with said inner and outer panels for releasably connecting each of said inner back wing sections with a respective outer front wing section to form a lower abdominal encasing structure.

6. The diaper according to claim 5 wherein said outer panel and said inner panel is disposed about an imaginary respective first and second longitudinal axis and said fastening means includes:
a pair of loop-fitted elongated fastening strips, one of said fastening strips being mounted on each of said inner panel back wings substantially perpendicular to said first longitudinal axis;
a pile fastening strip having a pair of conjoined, outwardly extending arms defining a substantially "V"-shaped configuration; said pile strip being mounted on said front wing section of said outer panel, to intersect said second longitudinal axis and to be bisected by said second longitudinal axis, said fastening strip forming a boundary whereby that portion of said outer panel positioned between said arms may be folded under thereby retaining said diaper out of contact with the navel region of an infant wearer.

7. The diaper according to claim 6 wherein a pair of elastic strips is associated with said connection strip, each strip being positioned on a respective side of said longitudinal axes.

8. A reusable, variable size diaper comprising:
an outer panel disposed about an imaginary longitudinal axis and having a perimeter, said outer panel having a configuration symmetrically arranged about said axis, said outer panel having a first pair of lateral extending wings joined to a second pair of lateral extending wings by means of an elongated connection strip interposed between said first and second pairs of wings, said outer panel being fabricated from a liquid impermeable fabric;
an inner panel having a second perimeter configured to have substantially an identical shape as said outer panel, said inner panel being essentially sealingly joined to said outer panel about the entire respective perimeters of said inner and outer panels, said inner panel being formed of a centrally position liquid permeable, fabric, section having a third perimeter, and a liquid impermeable fabric section positioned to circumscribe said liquid permeable fabric section about its third perimeter; whereby said joining of said inner and outer panels constitutes a fluid retaining sack; said sack being accessed substantially solely through said liquid permeable fabric section wherein liquid contacting said liquid permeable section is initially absorbed by said permeable section and any overflow is directed into said sack;
fastening means to detachably associate said first pair of wings with said second pair of wings to form a structure suitable for sealingly encasing the lower abdominal region of an infant.

9. A variable sized, reusable diaper comprising:
an outer panel having a first perimeter, said outer panel being disposed about a first imaginary longitudinal axis; said outer panel having a back portion possessing first and second laterally extending wing portions and a front portion possessing third and fourth laterally extending wing portions;, said outer panel being fabricated from a liquid impermeable, washable fabric;

a "V"-shaped attachment strip mounted on said front portion of said outer panel, said attachment strip extending from an edge of said first wing to said longitudinal axis and from an edge of said second wing to said longitudinal axis; said attachment strip having a plurality of upstanding ribs thereon defining a recess well between each pair of adjacent ribs;

an inner panel having a second perimeter, said inner panel being disposed about a second imaginary longitudinal axis, said inner panel having a back portion possessing a fifth and a sixth laterally extending wing corresponding in configuration to said first and second wing of said outer panel, said inner panel also having a front portion possessing a seventh and an eighth laterally extending wing corresponding in configuration to said third and fourth wings of said outer panel, said inner panel and outer panel being connected one to another about their respective corresponding perimeters, said inner panel being composed of a liquid absorbing elongated porous fabric strip positioned parallel with said second longitudinal axis and a liquid impermeable sheet mounted to circumscribe said liquid absorbing strip an association of said inner panel and said outer panel defining a hollow sealed impermeable sack having an interior cavity; said cavity being accessible through said porous absorbent strip wherein liquid contacting said absorbent strip in excess of said strip's ability to absorb said liquid is directed to said interior cavity and retained therein by said impermeable sack;

a pair of lever fitted fastener clips, one of said clips being mounted on each of said fifth and sixth wings of said inner panel, said fastener clips being adapted to slide along said attachment strips, wherein said fastener clips include a pivot mounted, lever actuated extension adapted to be manually inserted into a recess well of said attachment strip to form a manually releasable union of said clip with said attachment strip at a desired location along a length of said strip thereby releasably locking said clip onto said attachment strip at said location.

10. A variable sized, reusable diaper comprising:

an outer panel having a first perimeter, said outer panel being disposed about a first imaginary longitudinal axis; said outer panel having a back portion possessing first and second laterally extending wing portions and a front portion possessing third and fourth laterally extending wing portions; said outer panel being fabricated from a liquid impermeable, washable fabric;

inner panel having a second perimeter, said inner panel being disposed about a second imaginary longitudinal axis, said inner panel having a back portion possessing a fifth and a sixth laterally extending wing corresponding in configuration to said first and second wing of said outer panel, said inner panel also having a front portion possessing a seventh and an eighth laterally extending wing corresponding in configuration to said third and fourth wings of said outer panel, said inner panel and outer panel being connected one to another about their respective corresponding perimeters, said inner panel being composed of a liquid absorbing elongated porous fabric strip positioned parallel with said second longitudinal axis and a liquid impermeable sheet mounted to circumscribe said liquid absorbing strip an association of said inner panel and said outer panel defining a hollow sealed impermeable sack having an interior cavity; said cavity being accessible through said porous absorbent strip wherein liquid contacting said absorbent strip in excess of said strip's ability to absorb said liquid is directed to said interior cavity and retained therein by said impermeable sack; fastening means associated with said inner and outer panels for releasably connecting said first wing with fifth wing and said second wing with said sixth wing to form a structure for encasing the lower abdominal region of an infant.

* * * * *